United States Patent [19]
Carr et al.

[11] Patent Number: 5,824,292
[45] Date of Patent: Oct. 20, 1998

[54] ORAL CARE COMPOSITIONS

[75] Inventors: Stuart William Carr, Liverpool; Karen Marie Pickup, Spital; Philippa Margaret Smith, Millane; Kurt Matthew Schilling, Wirral, all of Great Britain

[73] Assignee: Quest International B.V., Naarden, Netherlands

[21] Appl. No.: 631,219

[22] Filed: Apr. 12, 1996

[30] Foreign Application Priority Data

Apr. 12, 1995 [EP] European Pat. Off. .............. 95302471

[51] Int. Cl.⁶ ............................ A61K 7/16; A61K 33/30; A61K 39/40
[52] U.S. Cl. .............................. 424/49; 424/87; 424/641; 424/643
[58] Field of Search ......................................... 424/49–58

[56] References Cited

U.S. PATENT DOCUMENTS

| | | | |
|---|---|---|---|
| 4,193,983 | 3/1980 | Ullman et al. | 424/12 |
| 4,342,739 | 8/1982 | Kakimi et al. | 424/1 |
| 4,820,649 | 4/1989 | Kawaguchi et al. | 436/501 |
| 5,049,375 | 9/1991 | Tsujita et al. | 424/52 |
| 5,059,416 | 10/1991 | Churvkiri et al. | 424/48 |
| 5,089,391 | 2/1992 | Buechler et al. | 435/7.1 |
| 5,130,146 | 7/1992 | Tsujita et al. | 424/52 |
| 5,169,754 | 12/1992 | Siiman | 435/5 |
| 5,244,651 | 9/1993 | Kayane et al. | 424/49 |
| 5,302,373 | 4/1994 | Giacin et al. | 424/49 |
| 5,330,749 | 7/1994 | Giacin et al. | 424/49 |
| 5,455,023 | 10/1995 | Giacin et al. | 424/49 |
| 5,466,609 | 11/1995 | Siiman et al. | 436/518 |
| 5,492,814 | 2/1996 | Weissleder | 435/725 |

FOREIGN PATENT DOCUMENTS

| | | | |
|---|---|---|---|
| 0 481 701 A1 | 4/1992 | European Pat. Off. | A61K 9/50 |
| WO 94/26245 | 11/1994 | WIPO | A61K 7/16 |

*Primary Examiner*—Shep K. Rose
*Attorney, Agent, or Firm*—Pillsbury Madison & Sutro LLP

[57] ABSTRACT

The invention relates to oral care compositions with colloidal anti-plaque agents which have been coated with particular polymers containing carbohydrate (saccharide) or peptide structures which are specifically recognised by bacterial adhesins, more particularly carbohydrate containing polymers recognized by bacterial lectins, or with antibodies or antibody fragments which recognize plaque bacterial antigens. Such coated colloidal anti-plaque agents, e.g. coated colloidal zinc oxide, can be target to specific sites in the human mouth where the anti-plaque agent is then released at acidic pH.

5 Claims, 3 Drawing Sheets

AF=ASIALOFETUIN
AN=A.NAESLUNDII
LAC=LACTOSE
GLU=GLUCOSE

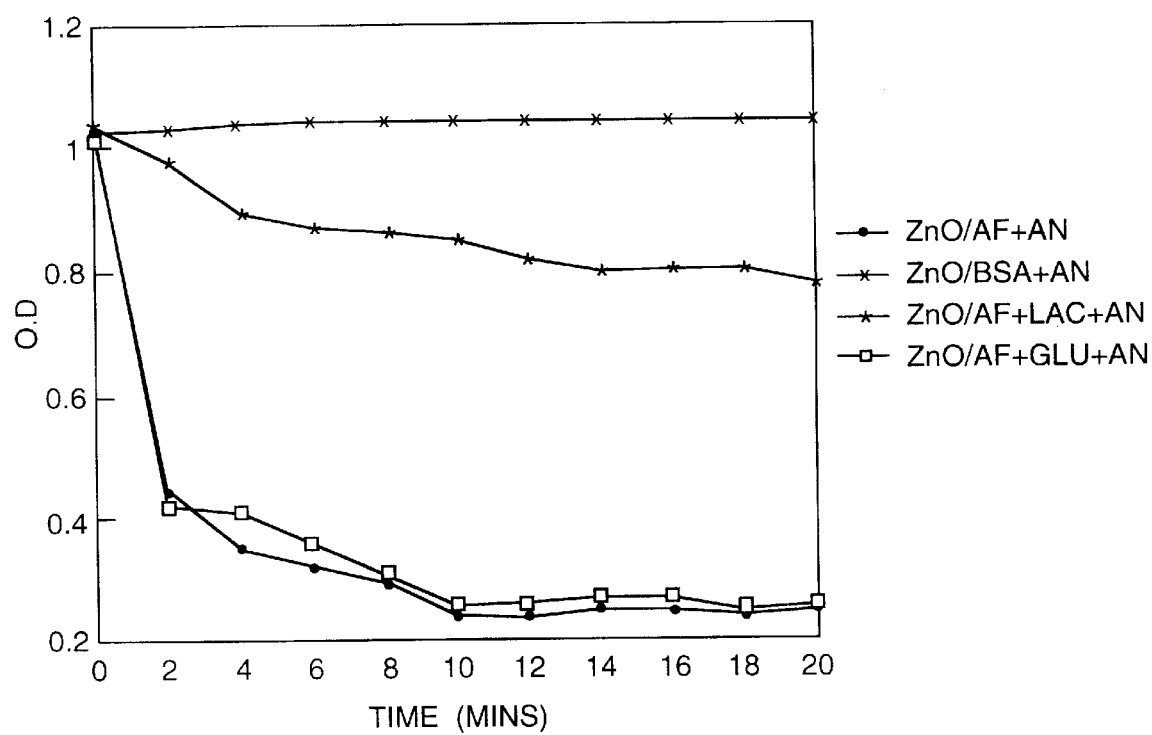

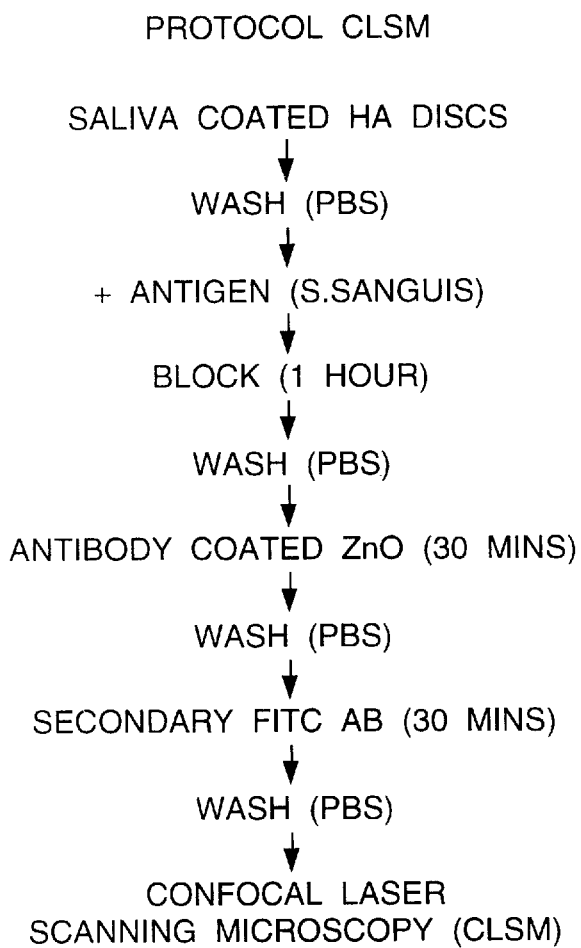

ORAL CARE COMPOSITIONS

FIELD OF THE INVENTION

The present invention relates to the delivery of colloidal anti-plaque agents to dental plaque by the use of (i) antibodies which specifically recognise plaque bacterial antigens (e.g. *Streptococcus sanguis, Streptococcus mutanes* etc) and/or (ii) polymers containing carbohydrate (saccharide) or peptide structures which are specifically recognised by bacterial adhesins, more particularly carbohydrate containing polymers recognized by carbohydrate binding proteins ie lectins. The invention also relates to oral care compositions comprising such delivery systems.

BACKGROUND OF THE INVENTION

The adherence of bacteria to the enamel pellicle and the polysaccharides that they metabolise generally leads to the development of plaque (a microbial community embedded in polymers of salivary and bacterial origin) on the tooth surface. In the absence of good oral hygiene plaque can accumulate beyond levels compatible with oral health which frequently results in a disease state for example caries and gingivitis. Research to date suggests the microbial colonioation is enhanced by stereospecific interactions between cell surface proteins referred to as 'adhesins' and cognate binding sites present for example on other bacteria or on host tissue (Teivion Y and Sharon N(1981) Biochim. Biophys. Acta 642,336; Kawai Y and Yano I (1983) Eur. J. Biochem. 136, 351; Mirelman D and Ofek I (1986) In: *Microbial Lectine and Agglutinins,* Mirelman D. Ed., John Wiley and Sons. Indeed, many oral species have been shown to possess adhesins which are typically lectins ie carbohydrate binding proteins (Levine et al., 1978 Infect. Immun. 19, 107; Weerkamp and McBride, 1980 Infect. Immun. 30, 150). Oral bacterial lectins which mediate attachment to carbohydrate structures present on pellicle, plaque matrix and bacterial surfaces undoubtedly enhance the development of plaque.

The present invention relates to the targeted delivery of colloidal anti-plaque agents to the tooth surface. The term "anti-plaque agents" as used herein covers antimicrodial agents which kill certain oral bacteria such as *S. sanguis* or *S. mutans,* as well as agents that prevent or reduce plaque formation in another way, e.g. by influencing plaque pH or by forming antimicrobial agents in situ. Typical examples of antimicrobial agents are antimicrobial metals and metal oxides, such as silver, copper, zinc, iron, tin, mercury, lanthanum, yttrium, indium, gold. A preferred antimicrobial agent is zinc oxide, and the invention will be further discussed and illustrated on the basis of zinc oxide, it being understood, however, that the invention is not limited thereto.

Examples of other anti-plaque agents are plaque-pH buffering agents such as chalk, and agents that form antimicrobial agents in situ, e.g. oxidoreductases, which are absorbed onto a colloidal carrier material such as colloidal silica.

Colloidal zinc is potentially a dual functional agent where the release of zinc ions at acidic pH results in (i) inhibition of microbial glycolysis and (ii) a buffering effect. An additional advantage of using colloidal zinc oxide is its small particulate plaque and as 10 nm), which enhances its diffusion through plaque and as a consequence its efficacy. Particulate zinc oxide can be targeted to a specific site by e.g. (i) polymers, particularly glycoproteins and other saccharide or oligosaccharide containing adducts, and (ii) antibodies.

Several studies have illustrated the anti-plaque activity of zinc and zinc oside and the ability of the zinc ion to inhibit microbial glycolysis (e.g. Gilbert R J and Ingram G S (1988) J. Pharm. Pharmacol. 40, 399; Schele A A; Assar S and Kolla G (1988) APMIS 96,761; JP 4038904; WO 8700051 and DE 3681289). However, colloidal zinc oxide has not been proposed for this purpose nor has it been suggested to deliver it to a site by a specific targeting system. Another proposed dental application includes the use of zinc oxide as a hardenable and/or cushioning material for treatment of caries (e.g. No. EP 329 098; SU 1648473). Also, zinc oxide has been proposed as a carrier of monoclonal antibodies in diagnostic methods (.e.g. JP 5010952).

One of the major technical problems associated with the development of effective active systems for oral care benefits is obtaining substantive delivery of the active to the desired site. Most anti-plaque agents which are currently used bind to oral surfaces via (i) electrostatic and/or (ii) hydrophobic interactions. However, this binding is generally reversible and non-specific in nature, ie agents will bind to all oral tissues. The substantially of the actives of the present invention will be enhanced by specific targeting to sites which can serve as anchor points within the mouth, followed by controlled release of zinc ions at an acidic pH.

Complexes can be formed between colloidal zinc oxide and the targeting system: eg antibodies, polymers. Compounds can be targeted to the tooth surface to control the development of bacteria associated with caries. Targeting and thus substantivity leads to a reduced amount of 'active' required. The targeting groups can be generated by synthetic chemistry (eg polymers, antibodies), purification or extraction from natural sources (eg. milk proteins) or through the tools of molecular biology (eg. antibodies and fragments).

DETAILED DESCRIPTION OF THE INVENTION

The purpose of the present invention is to upon specific targeting systems (eg. polymers, antibodies) for the substantive delivery of colloidal anti plaque agents, more particularly zinc oxide, to plaque bacteria.

In the case of a polymer targeting system, polymers which contain structures specifically recognised by bacterial adhesions are used to deliver zinc oxide. This is achieved by coating zinc oxide particles with the polymer. Such polymer targeting systems include natural or synthetic polymers containing saccharide or peptide structures specifically recognised by bacterial adhesins. Synthetic polymers include polyanionic, polycationic, or amphoteric adducts with: i) specific saccharides or oligosaccharides residues such as lactobionamide, maltobionamide, and other sugar structures; or ii) peptide structures. Natural polymers include dextrans, starches, bovine glycoproteins, plant glycoproteins and polysaccharides, and other natural macromolecules with sugar groups recognised by plaque bacteria. Furthermore, mixtures of proteins can be used to deliver colloidal metal oxide complexes. Suitable polymers include eg. dextrane (mentioned above), fetuin, food grade glycoprotein from bovine milk such as κ-casein, asialo-κ-casein, sweet whey, and asialofetuin.

In the case of an antibody targeting system an antibody or antibody fragment will bind to a target site (for example antibodies raised against *S. sanguis, S. mutans* will bind to their respective antigen ie *S. sanguis, S. mutans*). Antibody targeting systems include whole antibodies or monovalent or polyvalent fragments of antibodies which are derived synthetically or using molecular biology and natural production systems such as fermentation. Complexes may be formed through chemical complexation between anti-bacterial antibodies (fragments) and colloidal zinc oxide. Alternatively, a fusion can be made which consists of the antibody fragment binding region and colloidal zinc oxide. Antibody fragment fusions with peptide structures which adsorb efficiently to colloidal metal oxide complexes can also be used. Furthermore, self assembly systems can be utilised to target colloidal metal oxides, whereby a primary plaque-specific antibody or fragment is utilised to target plaque structures, and secondary antibodies (or fragments) specific for the first antibody (or fragment) are used to coat the metal oxide complex. In this way the dual antibody systems assemble in situ to target the complex to specific structures in dental plaque.

Another object of this invention is to use polymers which contain carbohydrate residues, specifically recognized by bacterial lectins, to target colloidal zinc oxide to a specific site and release zinc ions at an acidic pH. Another object of this invention is to use antibodies which recognise plaque bacteria to target colloidal zinc oxide to a specific site and release zinc ions at acidic pH.

Targeted colloidal zinc oxide described herein can be formulated into dentrificies, mouthrinses, gels, dental flosses and other oral case products. The oral care products can be in the form of toothpastes, gels, mouthwashes, powders, gargles, lozenges, chewing gum and the like.

The oral composition may furthermore comprise conventional ingredients, such as pharmaceutically acceptable carriers like starch, sucrose, polyols, surfactants, water or water/alcohol systems etc. When formulated into a dentifrice, such formulation may contain all the usual dentifrice ingredients. Thus, they may comprise particulate abrasive materials such as silicas, aluminas, calcium carbonates, dicalciumphosphates, hydroxyapatites, calcium pyrophosphates, trimetaphosphates, insoluble hexametaphosphates and so on, usually in amounts between 5 and 60% by weight.

Furthermore, the dentifrice formulations may comprise humectants such as glycerol, sorbitol, propyleneglycol, latitol and so on.

Surface-active agents may also be included such as anionic, nonioinic, amphoteric and zwitterionic synthetic detergents. Examples thereof are sodium lauryl sulphate, sodium dodecylbenzenesulphonate, sodium mono- and dioctylphosphate, sodiumlauroylsarcosinate, cocamidopropylbetain.

Binders and thickeners such as sodium carboxymethylcellulose, xanthan gum, gum arabic etc., may also be included, as well as synthetic polymers such as polyacrylates and carboxyvinyl polymers such as Carbopol®.

Flavours such as peppermint and spearmint oils may also be included, as well as preservatives, opacifying agents, colouring agents, pH-adjusting agents, sweetening agents and so on.

Additional anti-bacterial agents may also be included such as Triclosan, chlorhexidine, copper, zinc- and stannous salts, such as copper sulphate, zinc citrate and stannous pyrophosphate, sanguinarine extract, metronidazole. Further examples of additional anti-bacterial agents are quaternary ammonium compounds such as catylpyridinium chloride; bis-guanides such as chlorhexidine digluconate, hexetidine, octonidinc, alexhidine, halogenated bisphenolic compounds such as 2,2'methylenebis-(4-chloro-6-bromophenol).

Polymeric compounds which can enhance the delivery of active ingredients such as the anti-bacterial agents can also be included. Examples of such polymers are copolymers of polyvinylmethylether with maleic anhydride and other similar delivery enhancing polymers, e.q. those described in DE-A-3,942,643 (Colgate).

Furthermore anti-inflammatory agents such as ibuprofen, flurbiproten, aspirin, indomethacin etc., may also be included.

Anti-caries agents such as sodium- and stannous fluoride, aminefluorides, sodium monofluorophosphate, calcium lactate and/or calcium glycerophosphates, strontium salts and stronitium polyacrylates, casein and casein digests and phosphorproteins may also be included.

Other optional ingredients include vitamins such as Vitamin C, plant extract, potassium salts such as potassium citrate, potassium chloride and potassium nitrate.

Other optional ingredients include enzyme such as dextranase and/or mutanase, amyloglucosidase, glucoseoxidase with lactoperoxidase, neuraminidases, and hydrogen peroxide generating compounds such as potassium peroxydiphosphate.

Furthermore, the oral compositions may comprise anticalculus agents such as alkali metal pyrophosphates, hypophosphite-containing polymers, organic phosphonates, phosphocitrates, etc.

Other optional ingredients that may be included are e.g. bacteriocine, bacteriophages, tissue respiratory factors, antibodies, bleaching agents such as peroxy compounds, effervescing systems such as sodium bicarbonate/citric acid systems, colour change systems, and so on.

The present invention will be further illustrated by way of the examples, of which Example 1 only confirms binding studies of various micro-organisms to various polymers reported in the literature, and the drawings.

BRIEF DESCRIPTION OF THE DRAWINGS

FIG. 2 and 3 arc also graphs comparing OD over time for the conditions indicated; and FIG. 4 illustrates the steps involved in an immunofluorescent method used herein.

EXAMPLE 1

Carbohydrate (polymer) Target System

Figure 1:
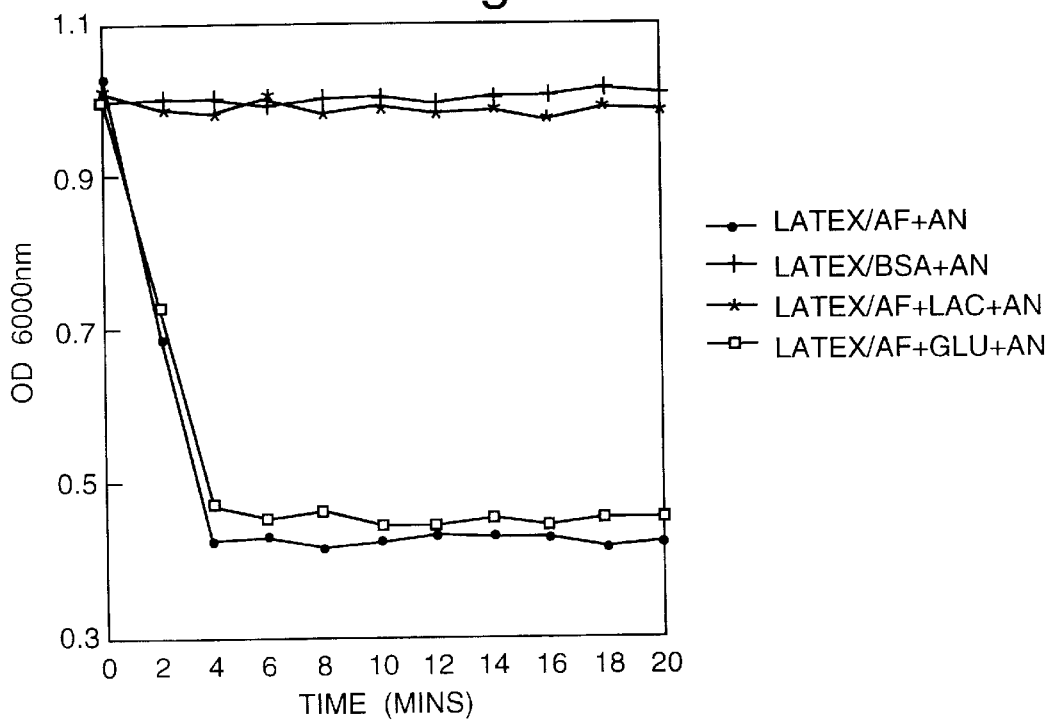
FIG. 1 is a graph comparing optical density (OD) over time, a reduction in OD representing an increase in bacterial agglutination.

1) Selection of a polymer to coat zinc oxide.

Several agglutination assays (1.1.1.2) were used to study well documented lectin-receptor interactions of *Actinomyacs naeslundii*, *Streptococcus sorbrinus* and *Streptococcus sanguis* (as illustrated in Table 1). Essentially, these assays monitor optical density (OD) over time where a reduction in OD correlates with an increase in bacterial agglutination, indicative of a lectin-receptor interaction.

Table 1: Carbohydrate structures present in certain polymers which are recognised by lectins of the three oral species.

TABLE 1

| Bacterium | Carbohydrate Structure Lectin For ----------> | Polymer |
|---|---|---|
| S. sohrinus | α 1.6 glucose residues | Doxtrans >70 KDa |
| S. sanguis | N-acetyl neuraminic acid (sialic acid) | Fetuin |
| A. naeslundii | β-galactose | Asialofetuin |

1.1 Latex Bead Agglutination

This assay was used to study surface binding of a *A. naeslundii* and *S. sanguis* to polymer coated beads.

(i) Preparation of micro-organisms

Cultures of *A. naeslundii* PK 29, *S. sanguis* C9B and *S. sobrinus* 6715 were grown up overnight at 37° C. in brain heart infusion supplemented media (brain heart infusion 47 g/l, yeast extract 5 g/l; cysteine HCL 0.1 g/l; haemin 500 ml/l; vitamin K 5 mg/l; sterile horse blood 50 ml/l). Bacterial cultures were then centrifuged (200 g; 10 minutes), washed twice in phosphate buffered saline (PBS) and resuspended in PBS to an appropriate absorbance at 600 nm.

(ii) Preparation of polymer coated latex beads

200 μl of latex beads (diameter 6.4 μ, Sigma, Catalogue No. SD-6A) were dispensed into a polypropylene tube (Greiner) containing a 20 mM Trixma based (Sigma) buffer, pH 8.2 (0.75% glycine; 1% sodium chloride; 0.1 mM calcium chloride and 0.02% sodium azide 'TGS') and 5 mg of an appropriate coating glycoproptein (ie asialofetuin : *A. naesludnii*; fetuin : *S. sanguis*). The sample was incubated at 37° C. for 1 hour on a rotary mixer (60 rpm. Heidolph) and then washed and centrifuged three times in TGS buffer 0.1% bovine serum albumin (BSA). Finally, the deposit was resuspended in 10 ml of 0.1% BSA/TGS buffer.

(iii) Assay procedure

Disposable polystyrene cuvettes with sealable plastic caps (Sigma Aldrich Techware) containing a total sample volume of 2.0 ml were used, 1.0 ml of latex treated (asialofetuin or fetuin) beads were placed in the cuvette followed by an appropriate amount of TGS. Finally, 0.1 ml of the bacterial suspension * (*A. naeslundii* or *S. sanguis*) was added to initiate agglutination. The cuvettes were sealed and agitated prior to an initial absorbance reading.

Subsequent readings were taken at two minute intervals for a twenty minute period (OD 600 ml), Cuvettes were rotated at 25 rpm between readings.

* Final OD (600 nm) of bacterial suspensions was 1.0.

NB. Control samples contained latex beads which were coated with the non carbohydrates protein BSA which would not be recognisd by the bacterial lectin. Specificity of the reaction was determined by incorporating lactose, a β-galactoside, which competes for the bacterial lectin site on *A. naeslundii* and inhibits agglutination.

Results

Incubation of asislofetuin treated latex beads with *A. naeslundii* resulted in a large drop in absorbance with a concomitant increase in agglutination (FIG. 1). Here, bacterial agglutination was attributed to interaction of the bacterial lectin with multiple β-galactose structures on the latex beads. Specificity of the bacterial binding is indicated by the lactose results where the addition of lactonse, which completes for the bacterial lectin site, appears to have bound to the lectin site on *A. naeslundii* and inhibited bacterial agglutination. Glucose which does not compete for the lectin site had little or no affect on bacterial agglutination.

When *S. sanguis* was added to fetuin coated latex beads there was little/no bacterial agglutination. This was an unexpected result as *S. sanguis* has a well documented lectin for sialic acid residues, in this instance purported to be present in fetuin. The lack of agglutination is most likely attributed to the manufacturing process of fetuin where a large proportion of the terminal sugar is sialic acid may have been cleaved off and lost in the process.

1.2 Polymer-Induced Agglutination

This assay was used to study glucan binding of *S. sobrinus* where bacterial agglutination would be expected to occur if recognition occurred between α-1,6 linked glucose residues in dextrans of greater than 70KDa and the lectin of *S. sobrinus*.

Assay procedure

Disposable cuvettes, as before, were used for this assay, 0.2 ml of 5% BSA in PBS was dispensed into a cuvette followed by the addition of 1.6 ml of bacterial suspension*. The agglutinin (dextrans >70 KDa, in this instance 79 KDa and 2000 KDa) was then added to the suspension which was brought to a total volume of 2.0 ml by the addition of PBS. The cuvettes were sealed and agitated prior to an initial absorbance reading. Subsequent readings were taken at two minute intervals for a twenty minute period (OD 600 nm). Cuvettes were rotated at 25 rpm between readings. Controls included (a) bacteria without dextran and (b) bacteria with dextrans of >70 KDa where bacterial agglutination would not be expected.

* Final OD (600 nm) of bacterial suspensions was 1.0.

Results

Figure 2:
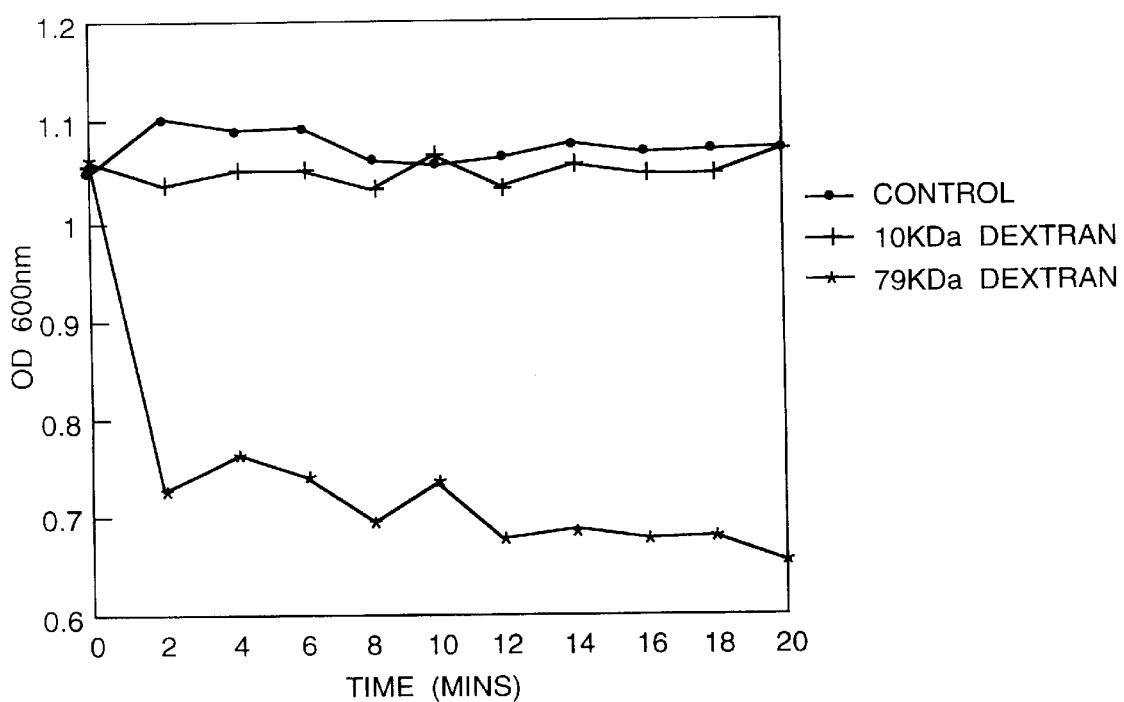

The addition of *S. sobrinus* to dextrans of 79 KDa and 2000 KDa caused a drop in absorbance which corresponded to an increase in bacterial agglutination (FIG. 2). This response suggested lectin recognition of glucose residues in dextrans of greater than 70 KDa. No bacterial agglutination was observed when *S. sorbinus* was added to dextrans of less than 70 KDa. Dextrans less than ca. 70 Kda are presumably not large enough to crosslink multiple bacteria and therefore are not expected to induce agglutination.

1.3 Polymer Selection

The polymer selected to coat ZnO, on the basis of the above studies, was one that resulted in rapid, specific agglutination. The polymer found to meet such criteria was the β-galactose containing glycoprotein asialofetuin as depicted in FIG. 1.

EXAMPLE 2

Bacterial targeting of zinc oxide with β-galactose containing glycoprotein (asislofetuin)

2.1 Agglutination Assay

Method (i) Preparation of colloidal zinc oxide (primary particle size of ca.10 nm)

A coordination precursor complex to zinc oxide was synthesised by refluxing a 0.1M solution of $Zn(OAc)_3 2H_2O$ in ethanol for 3 hours. The solution was cooled to 0° C. prior to the addition of an ethanolic solution of NaOH which made the final concentration of base 0.1M. The solution was stirred for 1 hour and then evaporated to dryness. The resulting white solid was washed with distilled water, freeze dried and calcined at 160° C. to remove any loosely bound organics, particularly acetic acid.

(ii) Preparation of asialofetuin coated zinc oxide

Asialofetuin (0.02%) was added to a 0.03% solution of zinc oxide in distilled water and shaken on a roller mixer (Denley, Spiranmix 5) overnight (RT).

(iii) Assay procedure

Polystyrene cuvettes containing a total sample volume of 2.0 ml were used 1.0 ml of asialofetuin coated zinc oxide was placed in the cuvette followed by an appropriate amount of TGS buffer. The bacterial suspension* (0.1 ml of *A. naeslundii* or *S. sanguis*) was then added to initiate agglutination. The cuvettes were sealed and agitated prior to an initial absorbance reading. Subsequent readings were taken at two minute intervals for a twenty minute period (OD 600 nm). Cuvettes were rotated at 25 rpm between readings.

*Final OD (600 nm) of bacterial suspensions was 1.0.

NB. Control samples contained zinc oxide which was coated with the non-carbohydrate BSA which would not be recognised by the above bacterial lactine.

Specifically was determined by the addition of lactose which competes for the bacterial lectin site and as a consequence inhibits agglutination.

Results

Results indicated a specific interaction (ie lactose inhibitable) between the bacterial lectin of *A. naeslundii* and the β-galactose structures on the asialofetuin coated zinc oxide as illustrated in FIG 3.

2.2 Transmission Electron Microscopy (TEM)

Method

TEM was used to visualise the association of zinc with *A. naeslundii* within bacterial aggregates. Samples of test (asialofetuin coated zinc oxide+*A. naeslundii*) and controls (BGA coated zinc oxide+*A. naeslundii*; asialofetuin+lactose+*A. naesludii*) were dispensed onto transmission electron microscopy gride prior to viewing on a JEOL 200CK TEM at 80 keV.

Results

There appeared to be a clear difference with respect to zinc deposition between the test and control samples where sparce zinc was observed in control samples compared to abundant zinc (glomerates up to 0.7 u) on and around bacterial aggregates in test samples. When samples were titrated (asialofetuin coated zinc oxide 1:4; BSA coated zinc coated 1:4) zinc was not observed in control samples.

Results illustrated the ability of β-galactose residues, present on asialofetuin, to target colloidal zinc oxide to a specific site on *A. naeslundii*.

FIG. 3 shows β-galactose specific agglutination of *A. naeslundii* by asialofetuin coated zinc oxide.

EXAMPLE 3

Delivery of zinc ions from asialofetuin coated ZnO

Method

*S. mutans* (an organism which produces acid from the metabolism of carbohydrates and has been associated with caries) was grown up overnight in BHI (15% $CO_2$, 37° C.) and an inoculum of this culture made into fresh BHI (diluted ⅓) containing 4% sucrose. Cultures were incubated (15% $CO_2$, 37° C.) and samples taken at time 0 and then at hourly intervals (up to 9 hours). An equal volume of the bacterial aggregate (ie asialofetuin coated zinc oxide and *A. naeslundii*) containing 2 mM of zinc oxide was added to the *S. mutans* suspension prior to incubation for up to 1 hours at 37° C. After this period samples were taken for pH determination and viable counts (CPU/ml).

Results

The addition of zinc oxide aggregates to cultured of *S. mutans* had very little effect on either pH or viable count until the culture pH dropped to pH 4.29. At this pH (7 hours growth) a significant effect on pH and viable count of *S. mutans* was observed where the addition of the zinc oxide aggregate resulted in an increase in culture pH from 4.29 to 5.45 and a reduction in viable count of *S. mutans* (tables 2 and 3).

TABLE 2

Effect of zinc oxide aggregate on culture pH of *S. mutans*

|  | Culture pH |
| --- | --- |
| Test (+2 mM ZnO) | 5.45 |
| Control (−2 mM ZnO) | 4.29 |

(No significant difference with respect to pH was observed if the ZnO aggregate was added to the culture of *S. mutans* for 10 minutes or for up to 1 hour).

TABLE 3

Effect of the zinc oxide aggregate on viable count of *S. mutans*.

|  | Viable Count | |
| --- | --- | --- |
|  | CFU/ml | Log |
| Test (+2 mM ZnO) | $2.4 \times 10^7$ | 7.38 |
| Control (−ZnO) | $4.2 \times 10^8$ | 8.62 |

The reduction in viable count of *S. mutans* (as shown in table 3) is probably due to inhibition of glucose metabolism as a consequence of zinc ion release at acidic pH.

EXAMPLE 4

Targeting of zinc oxide with antibacterial antibody 4.1 Methods (i) Preparation of antibody coated zinc oxide Colloidal zinc oxide (0.03% was added to a 0.25 mg/ml solution of antibacterial antibody (i.e. anti *Streptococcus sanguis* IgG) in Tris/Hcl buffer, pH 9.1. This suspension was mildly sonicated prior to end mixing on a rotary shaker (60 rpm, Heidolph) for 5 hours. The suspension was then washed and centrifuged (10,000 rpm: 20 seconds, Eppendorf centifuge) three times in Tris/HCl buffer to remove any excess antibody. Finally the pellet was resuspended in 1 ml of buffer and stored at 4° C.

(ii) Specificity of antibody coated zinc oxide

An immunofluorescent method which employs confocal laser scanning microscopy (CLSM) was used to determine specificity is the ability of the antibody coated zinc oxide to recognise its antigen (FIG. 4). This method which quantifies the antibody-antigen reaction by pixel intensity allows in-situ viewing of the sample. Briefly, the antigen (*S. sanguic:* prepared as in 1.1) was added to saliva coated hydroxyapatite discs prior to the addition of a blocking agent (BSA) to reduce non-specific reactions. The antibody coated zinc oxide was then added before the addition of a fluorescently labelled antibody (Vector). Finally, the discs were viewed under the CLSM where digital images were produced and quantification on the basis of pixel intensity (20 images/test) determined. Settings used on the CLSM were : pinhole 150; voltage 900; offset −10; magnification ×100.

4.2 Results

The antibacterial (*S. sanguis*) antibody coated zinc oxide appeared to be specific where the pixel intensity result indicated strong antigen recognition (table 4).

TABLE 4

|  | Antibody Binding Pixel Intensity* |
| --- | --- |
| *S. sanguis* antibody coated ZnO | 161.12 (+/−45.82) |
| Negative control (no anti-bacterial antibody) | 14.64 (+/−4.97) |

* = measure of florescence

EXAMPLE 5

Delivery of zinc ions from antibody-coated zinc oxide

5.1 Method

S. mutans was grown up overnight in BHI (15% $CO_2$, 37° C.) and an inoculum of this culture made into fresh BHI (diluted ⅓) containing 4% sucrose. Cultures were incubated (15% $CO_2$, 37° C.) and samples taken at time 0 and then at hourly intervals (up to 9 hours). An equal volume of antigen (S. sanguis; see 1.1 (i) for proparation) was added to the bacterial suspension followed by the antibody coated zinc oxide containing 2 mM of zinc oxide. Samples were then incubated for up to 1 hour at 37° C. After this period samples were taken for pH determination and visable counts (CPU/ml).

5.2 Results

Similar to the polymer delivery work (see Example 3) the addition of antibody coated zinc oxide to cultures of S. mutans had very little effect until the culture pH dropped to pH 4.32. At this pH (7 hours growth) a significant effect on pH and viable counts was observed where the addition of antibody coated zinc oxide resulted in an increase in culture pH from 4.32 to 5.92 and a reduction in viable count of S. mutans.

TABLE 5

Effect of antibody coated ZnO on culture pH of S. mutans

|  | Culture pH |
| --- | --- |
| Test (+2 mM ZnO) | 5.92 |
| Control (−ZnO) | 4.32 |

(No significant difference with respect to pH was observed if the antibody coated zinc oxide was added to the culture of S. mutans for 10 minutes or for up to 1 hour).

TABLE 6

Effect of antibody coated zinc oxide on viable count of S. mutans

|  | Viable Count | |
| --- | --- | --- |
|  | CFU/ml | Log |
| Test (+2 mM ZnO) | $6.5 \times 10^6$ | 6.81 |
| Control (−ZnO) | $2.9 \times 10^8$ | 8.46 |

The reduction in viable count of S. mutans (as shown in table 6) is probably due to inhibition of glucose metabolism as a consequence of zinc ion release at acidic pH.

We claim:

1. An anti-plaque agent suitable for oral use in an oral composition, characterized in that the anti-plaque agent is colloidal zinc oxide coated with a targeting system selected from the group consisting of polymers which contain carbohydrate structures which are specifically recognized by bacterial adhesins, peptide structures which are specifically recognized by bacterial adhesins, antibodies which recognize plaque bacterial antigens and antibody fragments which recognize plaque bacterial antigens.

2. An anti-plaque agent according to claim 1, wherein the polymer contains carbohydrate structures which are specifically recognized by bacterial lectins.

3. An anti-plaque agent according to claim 2, wherein the polymer is a milk glycoprotein selected from the group consisting of κ-casein, asialo-κ-casein, sweet whey, asialofetuin and mixtures thereof.

4. An anti-plaque agent according to claim 1, wherein the colloidal anti-plaque agent is coated with a targeting system selected from the group consisting of antibodies raised against oral bacteria and fragments of antibodies raised agent oral bacteria.

5. A method for the delivery of colloidal anti-plaque agents to a tooth surface comprising formulating a colloidal anti-plaque agent which is zinc oxide coated with a material selected from the group consisting of polymers which express carbohydrate structures specifically recognized by bacterial lectins, antibodies which recognize plaque bacterial antigens and antibody fragments which recognize plaque bacterial antigens into a formulation selected from the group consisting of dentifrices, mouthrinses, gels, dental flosses, toothpastes, mouthwashes, powders, gargles, lozenges and chewing gum and applying said formulation to specific sites in the human mouth to release the colloidal anti-plaque agent in-situ.

* * * * *